United States Patent
Sünwoldt et al.

(10) Patent No.: US 8,506,909 B2
(45) Date of Patent: Aug. 13, 2013

(54) DEVICE FOR RECEIVING A TEST SAMPLE

(75) Inventors: Olaf Sünwoldt, Berlin (DE); Detlef Knebel, Berlin (DE)

(73) Assignee: JPK Instruments AG, Berlin (DE)

( * ) Notice: Subject to any disclaimer, the term of this patent is extended or adjusted under 35 U.S.C. 154(b) by 0 days.

(21) Appl. No.: 11/659,374

(22) PCT Filed: Aug. 4, 2005

(86) PCT No.: PCT/DE2005/001395
§ 371 (c)(1),
(2), (4) Date: Sep. 14, 2007

(87) PCT Pub. No.: WO2006/012893
PCT Pub. Date: Feb. 9, 2006

(65) Prior Publication Data
US 2008/0163702 A1 Jul. 10, 2008

(30) Foreign Application Priority Data
Aug. 5, 2004 (DE) ............... 20 2004 012 394 U

(51) Int. Cl.
*G01N 21/03* (2006.01)
*G01N 21/35* (2006.01)

(52) U.S. Cl.
USPC ........... 422/560; 219/201; 219/385; 356/244; 422/500; 422/561

(58) Field of Classification Search
None
See application file for complete search history.

(56) References Cited

U.S. PATENT DOCUMENTS

| 3,620,596 | A | | 11/1971 | Binniings | |
|---|---|---|---|---|---|
| 4,441,793 | A | | 4/1984 | Elkins | |
| 4,974,952 | A | | 12/1990 | Focht | |
| 5,173,261 | A | | 12/1992 | Krause et al. | |
| 5,181,382 | A | * | 1/1993 | Middlebrook | 62/3.2 |
| 5,281,516 | A | * | 1/1994 | Stapleton et al. | 435/3 |
| 5,675,154 | A | | 10/1997 | Lindsay et al. | |
| 6,153,426 | A | | 11/2000 | Heimberg | |
| 6,233,093 | B1 | | 5/2001 | Arnold et al. | |
| 7,047,796 | B2 | * | 5/2006 | Lewis et al. | 73/105 |
| 2002/0154399 | A1 | | 10/2002 | Eastman et al. | |

FOREIGN PATENT DOCUMENTS

| EP | 0436338 A2 | 7/1991 |
|---|---|---|
| JP | 07-043372 A | 2/1995 |
| JP | 11-206366 A | 8/1999 |
| WO | WO 02/084210 A | 10/2002 |

* cited by examiner

Primary Examiner — Sally Merkling
(74) Attorney, Agent, or Firm — Smith Patent Office

(57) ABSTRACT

The invention relates to a device for receiving a test sample, particularly sample holders for combined examination of the test sample by a test procedure combined with another test procedure, which differs from the first test procedure, with a planar preparation component (1) in a transparent material with a preparation surface on which the test sample can be prepared, wherein a test path for the introduction of a test facility for carrying out the test procedure is formed on one side of the preparation component (1) and another test path for the introduction of a test facility for carrying out the other test procedure on the test sample is formed on an opposite side of the preparation component (1), wherein a supporting and covering element (3a) which has an aperture (5) through which the test path is formed is pressed against the preparation component (1) on one side (FIG. 1).

22 Claims, 4 Drawing Sheets

DEVICE FOR RECEIVING A TEST SAMPLE

CROSS REFERENCE TO RELATED APPLICATIONS

This application is a national stage application under 35 USC 371 of International Application No. PCT/DE2005/0013195 filed on Aug. 4, 2005, which claims priority to German Patent Application No. 202004012394.0 filed on Aug. 5, 2004. The disclosure of International Application No. PCT/DE2005/0013195 and German Patent Application No. 202004012394.0 are hereby incorporated by reference.

The invention concerns a device for receiving a test sample, particularly sample holders, for combined examination of the test sample by a test procedure combined with another test procedure which differs from the first test procedure.

STATE OF THE ART

Scanning probe microscopy (SPM) is a method of measuring surface properties, for example topology. Volumetric properties close to the surface can also be determined, e.g. the elasticity of a test sample. The scanning probe microscopy is frequently disadvantaged by the fact that chemical properties of the test sample cannot be determined. Optical methods, for example, are therefore very useful as complementary methods of examination. If the test sample is suitably prepared, fluorescence microscopy may, for example, provide information about where a molecule or group of molecules is located. The lateral resolution of this optical method is much lower than in scanning probe microscopy, but should be set as high as is technically possible. Scanning nearfield optical microscopy (SNOM), a sub-category of scanning probe microscopy, would, in principle, also be capable of so doing, but its application is much more complicated and the optical method also provides information from deeper layers of the sample.

To combine the methods of examination, it is frequently appropriate to apply decoupling by taking an inverse microscope and adapting SPM from above. In this way, both methods may be applied as usual. It is of great advantage to use a probe scanner, i.e. an appliance which moves a probe in all three possible directions in space whilst the sample undergoing examination remains stationary. The test sample itself and its environment, e.g. the sample holder, form an interface.

To optimise fluorescence microscopy, the test sample must be prepared on a standard cover slip, as standard lenses used for microscopy are matched to these. There are other optical methods in addition to fluorescence microscopy which provide high resolution and which require a sample holder in the form of a cover slip for optimum use. All such methods are referred to hereinafter in general as "optical methods".

A very simple and generally acknowledged realisation of a device for receiving a test sample to be examined, also known as a liquid cell, consists of cementing a cover slip to a petri bowl with a hole from below, so that the test sample is prepared from above on the cover slip and is thus accessible to scanning probe microscopy without any restrictions arising in respect of simultaneous usability of the optical method for examining the test sample.

As well as optical accessibility by using a cover slip, it is interesting for the purposes of most experiments that tests may be carried out in water, where setting the temperature and replacing the liquid, e.g. to set the pH, are very important. If cells are to be examined, the addition of $CO_2$ as a buffer is also very important, to create conditions which will support life, at least for a short time.

There are known solutions for all these requirements, some of which have also been combined with commercial appliances. However, the structure of such a device for receiving the test sample is complicated, because, for example, several components must be arranged and screwed together in a suitable way. Access by a scanning probe microscope from above is possible, but there are restrictions which are unacceptable. For example, it is not possible to achieve the potentially high lateral and vertical resolution of the scanning probe microscope in a commercial appliance, particularly where testing takes place in a liquid medium such as water or buffer, for example. A further major problem is thermal drift, whereby particularly drift perpendicular to the test sample may entail that the relatively small scanning range of a scanning probe microscope, of, for example, 15 μm, is exceeded and that the probe used for testing either loses contact with the test sample or even collides with it. Thermal drift in the sample plane is also problematic, as it is then particularly difficult to relocate a point on the sample if the test sample undergoes pronounced change due to a temperature fluctuation.

THE INVENTION

The object of the invention is to create a device for receiving a test sample, particularly sample holders, which has a simple structure and is convenient to use, for combined examination of the test sample using a test procedure, and another test procedure differing from the first test procedure. In addition, a slight drift distance between the test sample and particularly a probe of a scanning probe microscope must be guaranteed if the test sample is reproduced in a liquid medium of which the temperature can be set.

This object is solved by a device in accordance with independent claim 1. Advantageous embodiments of the invention form the subject of dependent sub-claims.

According to one aspect of the invention, a device for receiving a test sample, particularly sample holders, is created, for combined examination of the test sample with a test procedure and another test procedure which differs from the first test procedure, with a planar preparation component in a transparent material with a preparation surface on which the test sample can be prepared, wherein a test path for the introduction of a test facility for carrying out the test procedure is formed on one side of the preparation component and another test path for the introduction of a test facility for carrying out the other test procedure on the test sample is formed on an opposite side, wherein a supporting and covering element, which has an aperture through which the test path is formed, is pressed against the preparation component on one side.

By using the device, the test sample can be examined by two different test procedures, an originally available surface area of the preparation component being restricted to the size necessary for examination by using the supporting and covering element. Beyond the restrictive aperture, the preparation component is supported by the supporting and covering element, promoting as oscillation-free a bearing of the test sample as possible. In particular, oscillation of the preparation component in the direction of the supporting and covering element is minimised or even wholly suppressed.

In one embodiment, the surface of a cover slip used as a preparation component is restricted, as a resonant frequency of the cover slip is too low if it is only held by the edge and thus restricts the control cycle of a scanning probe microscope when examining the test sample. In this case, commercially available diameters of the cover slip, e.g. 24 mm, are preferably assumed. Other diameters which permit the adaptation of a lens for optimum examination are, of course, also possible.

The resonant frequency of the cover slip is reduced still further if a column of water rests on the cover slip as an additional mass. Tighter mounting of the cover slip on both sides is not advantageous, as access for the optical methods of examination, particularly with high-resolution commercial objectives, would no longer be possible as a result. However, restriction of the surface from above is possible and achieves sufficient stability. The reason for this lies in a restriction of the free upward oscillation, which prevents cover slip basic mode oscillation. A mounting may also be provided from below if a thin enough sheet is used, which is thinner than an operating distance. However, this embodiment is relatively complicated and more cost-intensive.

In one embodiment three components are provided: a bowl; formed, for example, by a trough, a seal and a cover slip; a support and a temperature element, which can, for example, heat and cool. Provision may also be made for the temperature element to heat only or cool only. The connections between these components are preferably formed as follows. As the central element, the bowl is connected to the temperature element so that it will conduct heat and with the support so that it will insulate from heat. This guarantees that the support which creates the physical connection to the remaining structure of the test apparatus will not be heated significantly and thus not display any thermal drift. The bottommost part of the bowl is formed by the cover slip on which the sample is prepared. This now lies on part of the support which insulates it from heat. As the support does not drift in the three directions in space, or only drifts very little, the part which lies on the cover slip will only drift a little. Vertical drift of the cover slip is thus reduced to its intrinsic thermal expansion due to the coefficient of expansion of glass. A change in temperature of the remaining bowl and the temperature element, and vertical drift caused thereby, takes place in relation to the non-drifting components and is therefore of no significance to the cover slip.

Drift of the preparation components preferably in the form of cover slips in the sample plane can particularly be prevented in an embodiment by forming the connection between the bowl and the temperature element by means of a turning and sliding joint. This can allow the temperature element to drift without this movement being transmitted to the trough and thus the entire bowl. Although the trough itself is also heated, it is mainly symmetrical to the central axis, to which it therefore drifts radially. A test sample in the middle of the cover slip thus only displays a slight drift in the sample plane. In addition, the sealing element, preferably made of silicon, prevents direct transmission of the movement of the trough to the cover slip, forming the function of a floating bearing.

The connection between the temperature element and the support may be designed as a tilting mechanism in one embodiment and then comprises two elements, a hinge and a catch. These are preferably poor conductors of heat. The hinge and/or the catch may, of course, also conduct heat and thus belong to the temperature element or the support. Heat insulation then has to take place by means of separate components.

The tilting mechanism as an embodiment of the connection between the heating element and the support has the advantage that simple, reliable operation is possible. In particular, it allows the rapid removal of the parts of which the bowl is formed. These come into contact with liquid, e.g. physiological buffers, and therefore have to be removable from the structure for the purposes of cleaning or replacement. A further advantage of the tilting mechanism is that a temperature sensor may be dipped into the liquid when it is tilted downwards. The sensor is thus always applied precisely to the same point and it is certain that it will not touch the wall of the bowl, for example. Such a malfunction would have to be anticipated if the user had to fit the temperature sensor personally after each assembly. In addition, more accurate control, e.g. by calibration, can be implemented by means of the precise positioning.

PREFERRED EMBODIMENT SAMPLES OF THE INVENTION

The invention is described in more detail below using sample embodiments with reference to figures of a drawing.

Figure 1:
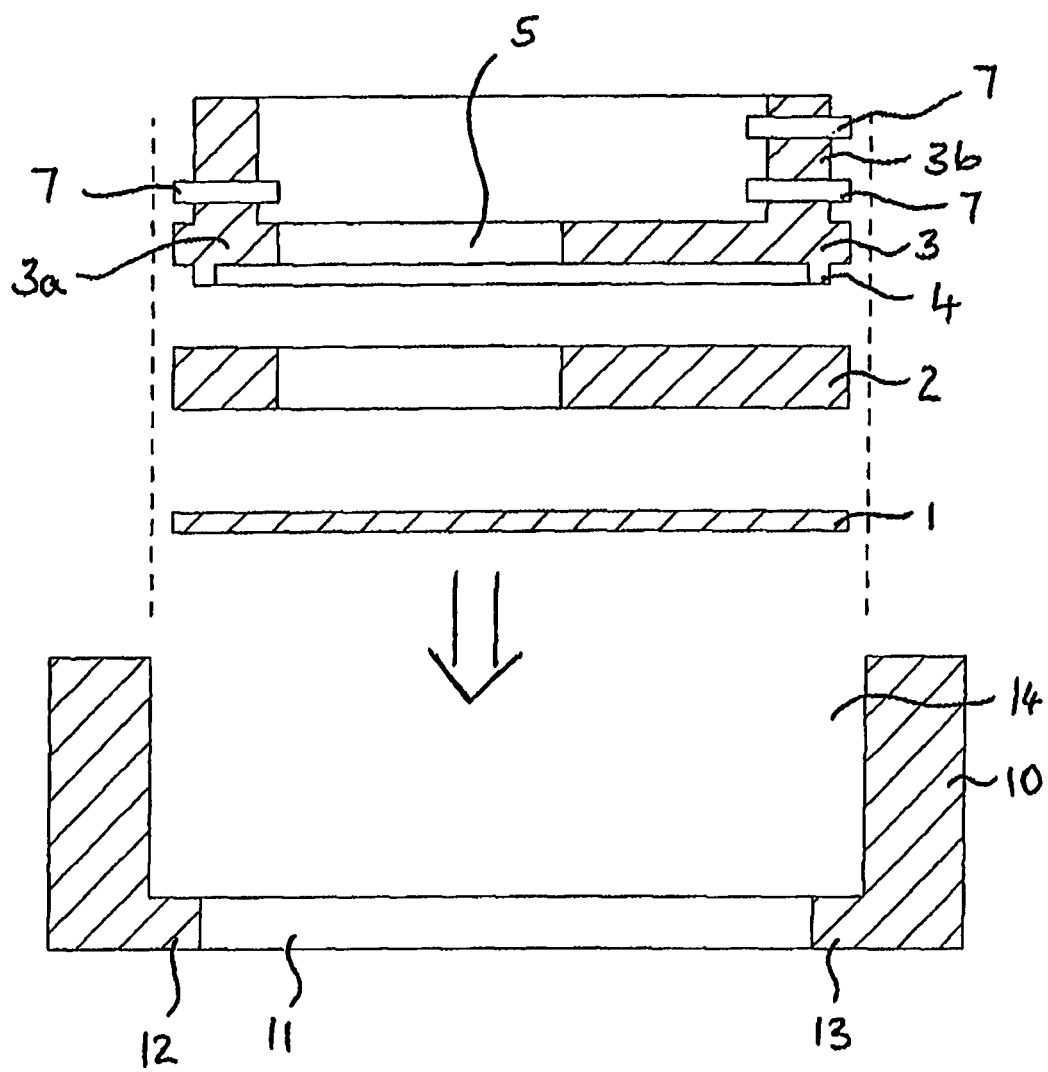
FIG. 1 is a cross-section of a device for receiving a test sample.

FIG. 1 shows components of a device for receiving a test sample in cross section. The device is integrated into test apparatus for examination of the test sample and makes it possible to examine the test sample by means of different test procedures. In accordance with FIG. 1, a preparation component in the form of cover slip 1 is arranged on a support 10. The support 10 has a support opening 11, which is demarcated by support sections 12, 13.

The cover slip 1 is preferably a commercially-available item. The cover slip 1 and the seal 2, which is, for example, in silicon, and a trough 3, together form a bowl which may be described as a liquid test cell and into which a liquid medium itself forming the test sample or at least partially enveloping the latter, may be poured, for example a buffer. The seal 2 and the trough 3 each have an aperture 5, which is preferably of the same size.

The trough 3 has a base 3a supporting/covering the cover slip 1 and a vessel wall 3b, and is preferably in stainless steel, but may also be in another heat-conducting material, e.g. tantalum. A chamber formed in the aperture 5 is extended to accommodate a test sample by using the vessel wall 3b. Provision may also be made for the trough 3 to be formed of several materials, if, for example, it is required that the part coming into contact with the liquid be of Teflon. Teflon can then be used inside and steel outside. If Teflon alone is used, no suitable temperature control is possible.

Sealing takes place by pressing the trough 3 against the sealing element 2 by a projection 4 formed in the area of the base 3a. In principle, it is possible to form the trough 3 as a thin hollow cylinder, but considerably higher stability of the scanning probe microscope can be achieved if the aperture 5 in the base 3a of the trough 3 is minimised so that the introduction of the scanning probe microscope from above along a test path extending through the aperture 5 is permitted and a practical range for displacement of the test sample is available.

Figure 2:
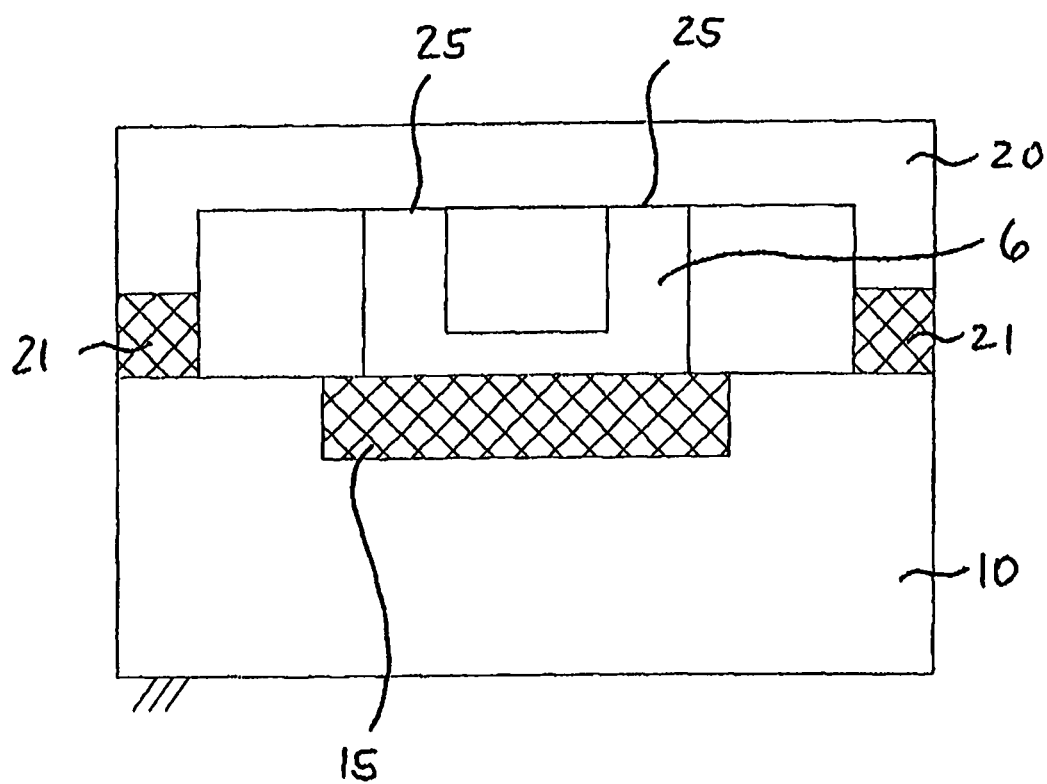
FIG. 2 is a schematic diagram to explain the minimisation of drift achieved.

In the area of the vessel wall 3b, the trough 3 has small tubes 7 through which liquid may be exchanged. It is purposeful for the depth of a depression 14 in the support 10 to be set so that all three components of the device are encompassed by a peripheral side wall of the depression 14, so that they cannot slip sideways on assembly. The three components, namely the cover slip 1, the seal 2 and the trough 3 form a bowl 6 (c.f. FIG. 2).

For the measurement, a test sample to be examined (not shown) is placed upon the preparation component 1 in the vicinity of the aperture 5 and is thus accessible to different test procedures from above and below.

FIG. 2 is a diagrammatic representation of the side of the device in accordance with FIG. 1, showing only elements which are necessary to explain the drift minimisation achieved. The bowl 6 stands upon the support 10. At least one portion 15 of the support 10 is made of a heat-insulating material. The entire support 10 may also be heat-insulating. However, this is usually more complicated in terms of manufacture and entails higher outlay for materials. A temperature element 20 for heating and/or cooling the test sample is also connected to the support 10 by heat-insulating components 21. A connection 25 between the temperature element 20 and the bowl 6 is a good heat-conducting connection, which may, for example, take the form of a turning and sliding joint.

In order to guarantee a good, heat-conductive connection, the structure may be designed so that sufficient pressure is exercised on the bowl 6 by the temperature element 20. This is ensured by compressing the seal 2 so that it works as a spring. The seal mentioned in connection with the explanations of FIG. 1 is also achieved by means of the pressure on the seal 2.

As already described above, the support 10 principally remains at room temperature, as it is thermally decoupled. The surface on which the bowl 6 rests will therefore not drift in any direction in space. The cover slip 1, which is in physical contact with the support 10 as the lowest part of the bowl 6, will thus drift in the vertical direction only as far as the coefficient of thermal expansion of glass and the thickness of the glass allow. Drift in the sample plane is, as aforementioned, mainly minimised by the turning and sliding joint, as movement of the temperature element 20 is transmitted to the bowl 6 to the lowest possible extent.

Figure 3:
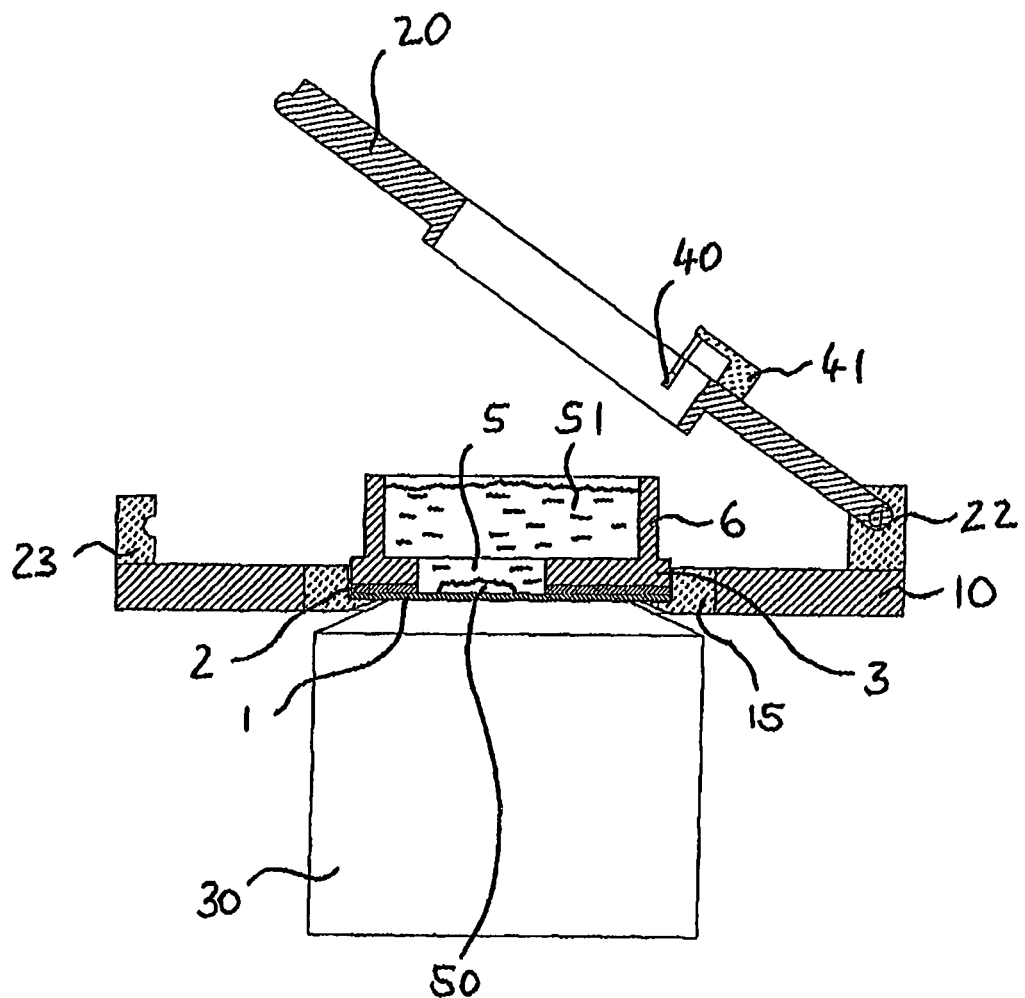
FIG. 3 is a cross-section of a further device for receiving a test sample, with a tilting mechanism.

FIG. 3 shows a further device for receiving a test sample in cross-section in which the connection between the temperature element 20 and the support 10 takes the form of a tilting mechanism. A hinge 22 and a catch 23 correspond to the heat-insulating components 21 in FIG. 2. The heat-insulating portion 15 of the support 10 is, for example, cemented to the support 10 and is formed so that access to the test sample by a lens 30 is possible along a further test path on the underside of the bowl 6. Optical examination of the test sample on the cover slip 1 is rendered possible by using the lens 30, in addition to scanning probe microscopy examination which can be carried out from above (see FIG. 1).

A temperature sensor 40 is fitted to the tilting mechanism, which is dipped into the liquid when tilted down. Other additional or alternative sensing apparatus may be fitted, e.g. for measuring the pH. Provision may be made for fitting several sensors simultaneously. The temperature sensor 40 is connected to the remaining structure by a heat-insulating component 41 so that the test result is not distorted. For the sake of clarity, the cover slip 1 is also shown with a test sample 50 and a liquid medium 51 are shown in FIG. 3.

Figure 4:
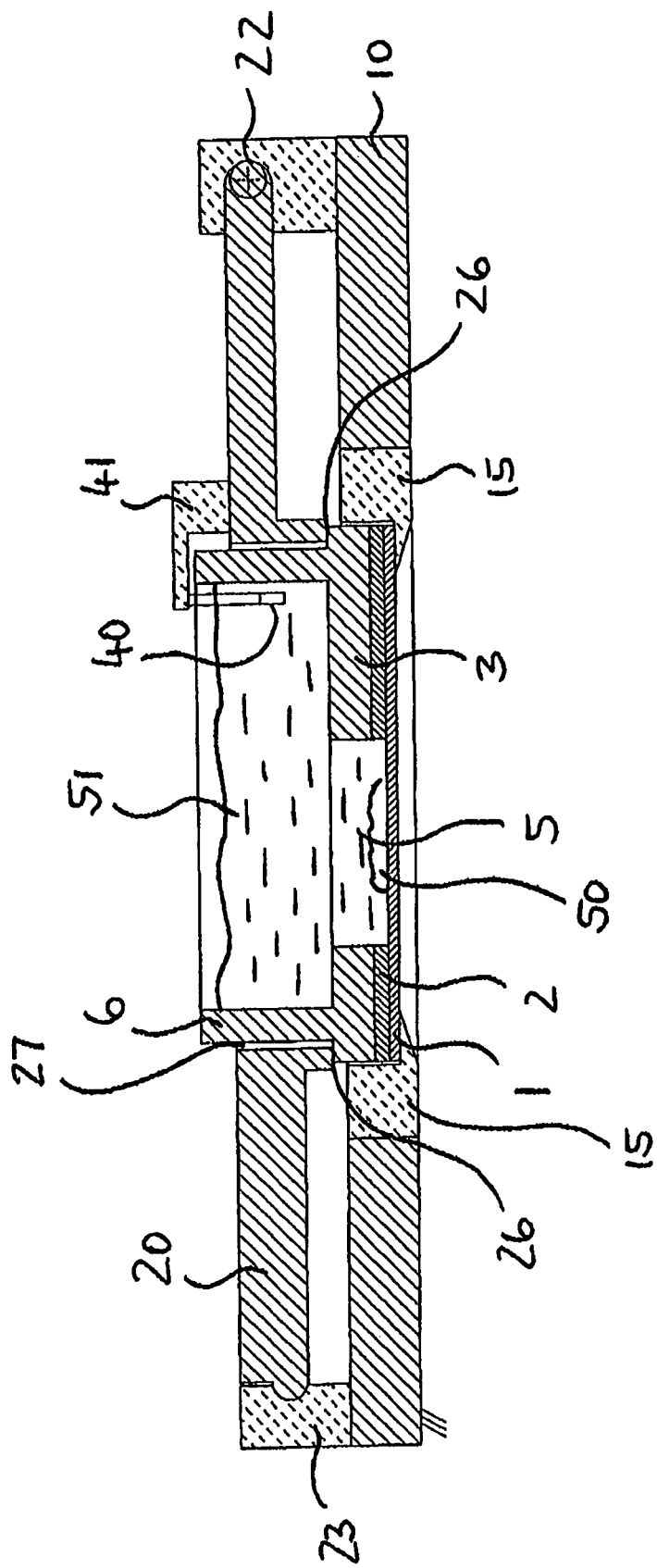
FIG. 4 is a device for receiving a test sample in accordance with FIG. 3, with the tilting mechanism tilted down.

FIG. 4 shows the further device for receiving a test sample in accordance with FIG. 3, with the temperature element 20 tilted down. In this embodiment, the pressure on the bowl 6 is exercised by compression of the seal 2. For this purpose, the hinge is designed so that the temperature element 20 touches the bowl 6 before engaging on a surface 26 and compresses the seal 2 when it engages. The surface 26 thus forms the aforementioned turning and sliding joint, so that movement of the bowl 6 is only restricted in the vertical direction. This is ensured if a distance 27, which represents the difference between the different radii, is greater than all the drift distances to be expected. The temperature sensor 40 is now dipped into the liquid medium 51.

The features of the invention, both individually and in any combination, disclosed in the above description, the claims and the drawings may be significant to the realisation of the invention in its various embodiments.

The invention claimed is:

1. A device for receiving a test sample, particularly sample holders, for combined examination of the test sample by a test procedure and another test procedure which differs from the first test procedure, with a planar preparation component in a transparent material with a preparation surface on which a test sample may be prepared, wherein a test path for the introduction of a test facility for carrying out the test procedure is formed on one side of the preparation component and another test path for the introduction of a test facility for carrying out the other test procedure on the test sample is formed on an opposite side of the preparation component and wherein a supporting and covering element which has an aperture through which the test path is formed, is pressed against the preparation component on one side;

wherein a sealing element is arranged between the preparation component and the supporting and covering element, to make a fluid-tight connection between the preparation component and the supporting and covering element;

the preparation component is located on a supporting component, which has a recess with a surface area which is larger than that of the aperture;

the sealing element is extending into an area overlapping with the recess in the supporting component; and wherein a peripheral vessel wall is arranged on the supporting and covering element, and the peripheral vessel wall forming an extended sample receiving chamber, the extended sample receiving chamber is disposed above the aperture.

2. The device in accordance with claim 1, wherein the aperture in the supporting and covering element encompasses the preparation surface.

3. The device in accordance with claim 2, wherein a reduced preparation surface is formed by the aperture of the supporting and covering element, which preparation surface is demarcated by the aperture.

4. The device in accordance with claim 1, wherein a sample receiving chamber is formed in the aperture of the supporting and covering element.

5. The device in accordance with claim 1, wherein a sealing aperture is formed in the sealing element, which has a diameter which is essentially equal to the diameter of the aperture in the supporting and covering element, the aperture and the sealing aperture being arranged to overlap.

6. The device in accordance with claim 1, wherein the preparation component and the supporting and covering element are thermally decoupled by the sealing element.

7. The device in accordance with claim 1, wherein one or more feed lines for introducing and removing a liquid to and from the extended sample receiving chamber are formed in the vessel wall.

8. The device in accordance with claim 1, wherein the vessel wall is formed in one piece with the supporting and covering element, forming a base component with the supporting and covering element.

9. The device in accordance with claim 6, wherein at least one of the supporting and covering element and the vessel wall have a coating, at least on the surface facing the extended sample receiving chamber.

10. The device in accordance with claim 1, wherein the preparation component is made of at least one of a glass and a transparent plastic material.

11. The device in accordance with claim 10, wherein the preparation component is a cover slip with standardized dimensions.

12. The device in accordance with claim 1, wherein the support is in a heat-insulating material, at least in one section in which the preparation component is used for support.

13. The device in accordance with claim 1, wherein a depression for receiving the preparation component and the supporting and covering element, and optionally the wall of the vessel, is formed in the support.

14. The device in accordance with claim 1, wherein at least one of the preparation component and the wall of the vessel are thermally coupled to a temperature element for at least one of heating and cooling the test sample.

15. The device in accordance with claim 1, wherein at least one of the preparation component and the wall of the vessel are retained by a swiveling holder, which can be swiveled between an open position and a closed position.

16. The device in accordance with claim 15, wherein the holder is retained by a catch in its closed position.

17. The device in accordance with claim 15, wherein at least one sensing apparatus is arranged to the holder, with which test conditions in the sample chamber can be detected in the closed position.

18. The device in accordance with claim 17, wherein at least one sensing apparatus is at least one of thermally decoupled from the holder, the wall of the vessel and the supporting and covering component.

19. The device in accordance with claim 15, wherein the temperature element is integrated into the swiveling holder and is thermally coupled to at least one of the preparation components and the vessel wall in the closed position.

20. The device in accordance with claim 14, wherein the temperature element is thermally coupled to at least one of the preparation component and the wall of the vessel by means of a turning and sliding joint.

21. The device in accordance with claim 1, wherein the test path is a scanning probe microscope test path for the introduction of a scanning probe microscope.

22. The device in accordance with claim 1, wherein the other test path is an optical test path for the introduction of an optical test apparatus.

* * * * *